(12) United States Patent
Takahashi et al.

(10) Patent No.: US 10,349,506 B2
(45) Date of Patent: Jul. 9, 2019

(54) MEDICAL IMAGING APPARATUS

(71) Applicant: Toshiba Medical Systems Corporation, Otawara-shi (JP)

(72) Inventors: Katsuo Takahashi, Nasushiobara (JP); Katsuyuki Tsukahara, Utsunomiya (JP); Junji Masahashi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 621 days.

(21) Appl. No.: 14/794,343

(22) Filed: Jul. 8, 2015

(65) Prior Publication Data

US 2015/0312999 A1    Oct. 29, 2015

Related U.S. Application Data

(63) Continuation of application No. PCT/JP2014/050160, filed on Jan. 8, 2014.

(30) Foreign Application Priority Data

Jan. 8, 2013   (JP) .................................. 2013-001258

(51) Int. Cl.
*H05G 1/32* (2006.01)
*H05G 1/10* (2006.01)
(Continued)

(52) U.S. Cl.
CPC ............. *H05G 1/32* (2013.01); *A61B 6/0457* (2013.01); *A61B 6/4007* (2013.01); *A61B 6/54* (2013.01);
(Continued)

(58) Field of Classification Search
None
See application file for complete search history.

(56) References Cited

U.S. PATENT DOCUMENTS

| 4,200,796 A | * | 4/1980 | Murakami | ................ G05F 1/14 378/102 |
| 2001/0012329 A1 | * | 8/2001 | Sato | ........................ H01J 35/10 378/93 |

(Continued)

FOREIGN PATENT DOCUMENTS

| JP | 53-078191 A | 7/1978 |
| JP | 05-056958 A | 3/1993 |

(Continued)

OTHER PUBLICATIONS

International Search Report dated Feb. 4, 2014 for PCT/JP2014/050160 filed on Jan. 8, 2014 with English Translation.

(Continued)

*Primary Examiner* — Hoon K Song
(74) *Attorney, Agent, or Firm* — Oblon, McClelland, Maier & Neustadt, L.L.P.

(57) ABSTRACT

A medical imaging apparatus includes an anode rotating type X-ray tube which generates X-rays, a high voltage generation unit implemented by circuitry which generates a high voltage to be applied to the X-ray tube, a power supply unit implemented by circuitry which supplies power to the high voltage generation unit, and a control unit implemented by circuitry which controls the high voltage generation unit to stop or start supply of a filament current to the X-ray tube and/or supply of a current to a stator coil for anode rotation in accordance with a predetermined rule.

12 Claims, 7 Drawing Sheets

(51) Int. Cl.
*A61B 6/00* (2006.01)
*A61B 8/00* (2006.01)
*A61B 6/04* (2006.01)
*H05G 1/02* (2006.01)
*H05G 1/36* (2006.01)

(52) U.S. Cl.
CPC .................. *A61B 6/56* (2013.01); *A61B 8/56* (2013.01); *H05G 1/025* (2013.01); *H05G 1/10* (2013.01); *H05G 1/36* (2013.01)

(56) References Cited

U.S. PATENT DOCUMENTS

2002/0131553 A1    9/2002  Tsuchino
2006/0233297 A1*  10/2006  Ishiyama ............... A61B 6/032
                                                    378/9

FOREIGN PATENT DOCUMENTS

| JP | 05-315091 A | 11/1993 |
| JP | 2001-178714 A | 7/2001 |
| JP | 2002-033064 A | 1/2002 |
| JP | 2002-272721 A | 9/2002 |
| JP | 2004-342360 A | 12/2004 |
| JP | 2010-46315 A | 3/2010 |
| JP | 2010-259581 A | 11/2010 |
| JP | 2011-024702 A | 2/2011 |
| JP | 2012-019856 A | 2/2012 |
| JP | 2012-100843 A | 5/2012 |

OTHER PUBLICATIONS

Written Opinion dated Feb. 4, 2014 for PCT/JP2014/050160 filed on Jan. 8, 2014.
Office Action dated Sep. 27, 2016 in Japanese Patent Application No. 2013-001258.
Office Action dated May 22, 2018 in Japanese Patent Application No. 2013-001258, 7 pages.

\* cited by examiner

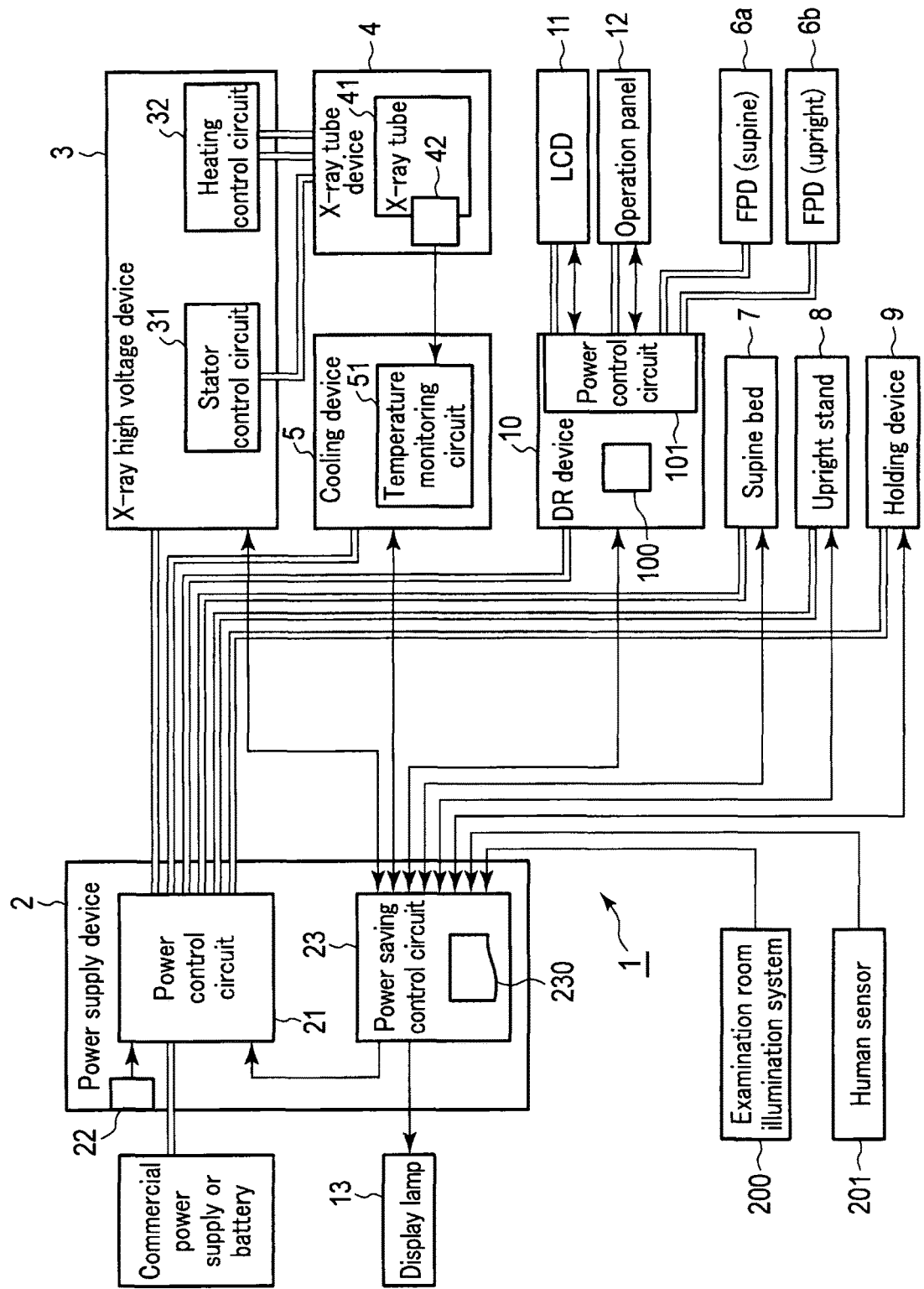
F I G. 1

| Power saving mode transition conditions | Power saving implementation methods |
|---|---|
| (a) No operation for predetermined time | (i) X-ray high voltage device; turning off stator output, lowering temperature of heated filament |
| (b) Any examination program being selected | (ii) Cooling device; intermittent driving, flow rate adjustment, stopping |
| (c) Processing other than processing from start of examination to end of examination being executed | (iii) FPD; turning off power |
| (d) Examination room not being used | (iv) Supine posture; turning off power |
| (e) Set time having arrived | (v) Upright stand; turning off power |
| (f) DR device being shut down | (vi) Holding device; turning off power |
| (g) Temperature of X-ray tube being less than threshold | (vii) DR device, standing by, shutting down |
| | (viii) LCD; turning off power, switching off backlight |
| | (ix) Whole system; turning off power (turning off commercial power supply or the like) |
| ---- | ---- |

FIG. 2

МЕDICAL IMAGING APPARATUS

CROSS-REFERENCE TO RELATED APPLICATIONS

This application is a Continuation application of PCT Application No. PCT/JP2014/050160, filed Jan. 8, 2014 and based upon and claims the benefit of priority from the Japanese Patent Application No. 2013-001258, filed Jan. 8, 2013, the entire contents of all of which are incorporated herein by reference.

FIELD

Embodiments described herein relate generally to a medical imaging apparatus which obtains a medical image representing the internal morphology of an object.

BACKGROUND

Conventionally, as medical imaging apparatuses which obtain a medical image representing the internal morphology of an object, there are known an X-ray diagnostic apparatus, X-ray CT (Computed Tomography) apparatus, MRI (Magnetic Resonance Imaging) apparatus, ultrasonic diagnostic apparatus, and the like.

A medical imaging apparatus like that described above is constituted by a plurality of devices. For example, an X-ray diagnostic apparatus includes devices such as an X-ray tube which generates X-rays, an X-ray detector which detects X-rays, a holding device which holds the X-ray tube, a supine bed used when imaging an object in the supine posture, an upright stand used when imaging an object in the upright posture, and a DR (Digital Radiography) device which executes various types of image processing. In general, these devices are arranged in the same examination room and operate upon receiving power from a common power supply device.

In general, once the main power supply of an X-ray diagnostic apparatus or medical imaging apparatus constituted by a plurality of devices as described above is turned on, the supply of power will not be interrupted even during waiting for imaging of an object. This leads to unnecessary power consumption.

BRIEF DESCRIPTION OF THE DRAWINGS

FIG. 1 is a block diagram showing the arrangement of the main part of an X-ray diagnostic apparatus according to an embodiment.

FIG. 2 is view showing examples of conditions for transition to a power saving mode and methods of implementing power saving according to this embodiment.

DETAILED DESCRIPTION

Figure 3:
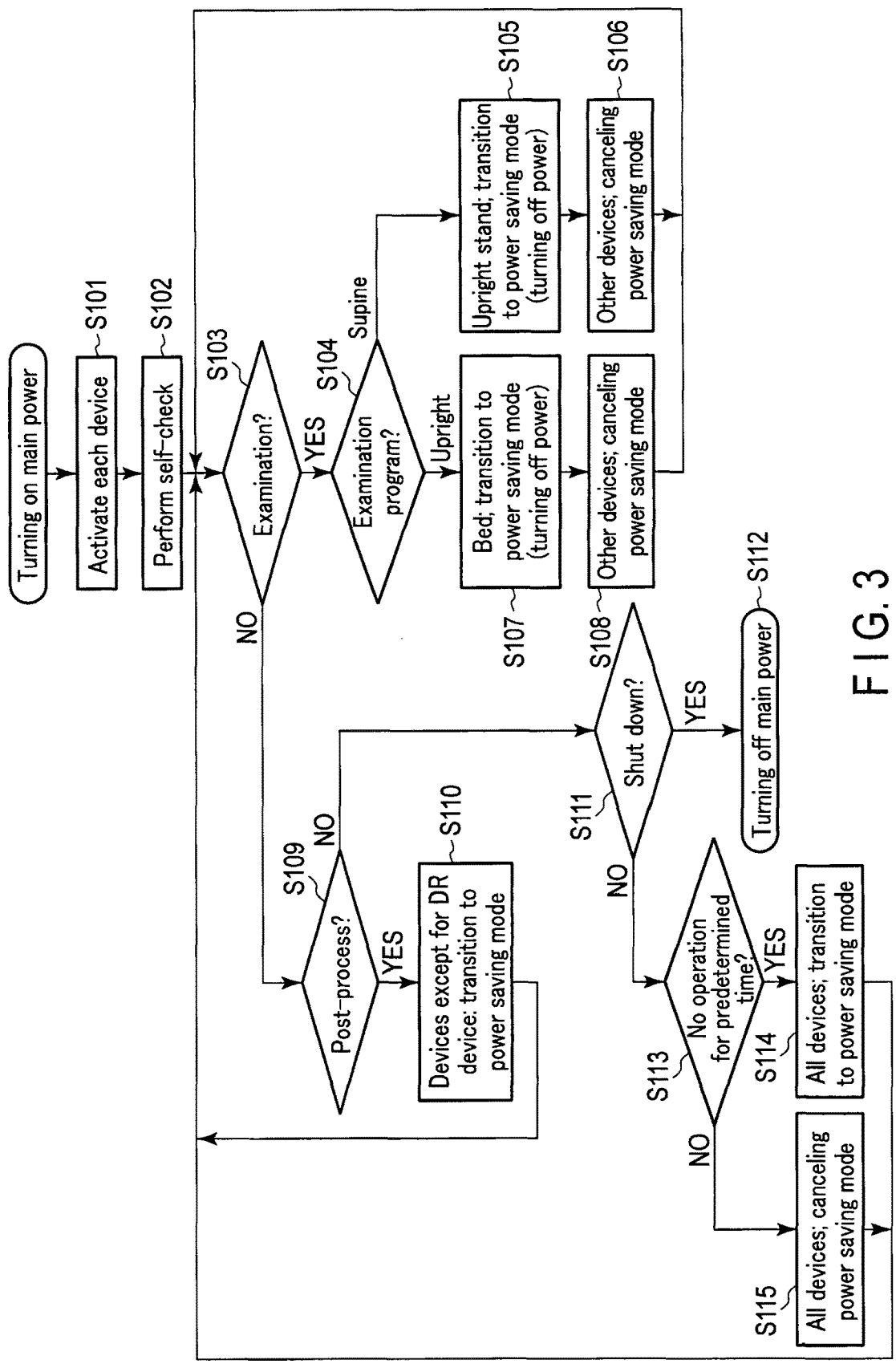
FIG. 3 is a flowchart for explaining the operation of the X-ray diagnostic apparatus in Specific Example 1.

A medical imaging apparatus includes an anode rotating type X-ray tube which generates X-rays, a high voltage generation unit implemented by circuitry which generates a high voltage to be applied to the X-ray tube, a power supply unit implemented by circuitry which supplies power to the high voltage generation unit, and a control unit implemented by circuitry which controls the high voltage generation unit to stop or start supply of a filament current to the X-ray tube and/or supply of a current to a stator coil for anode rotation in accordance with a predetermined rule.

An embodiment will be described below with reference to the accompanying drawings.

Note that this embodiment discloses an X-ray diagnostic apparatus as an example of a medical imaging apparatus.

[Arrangement of Main Part of X-Ray Diagnostic Apparatus]

FIG. 1 is a block diagram showing the arrangement of the main part of an X-ray diagnostic apparatus 1.

The X-ray diagnostic apparatus 1 shown in FIG. 1 is a so-called general imaging system, and includes a power supply device 2, an X-ray high voltage device 3, an X-ray tube device 4 (X-ray tube), a cooling device 5, FPDs (Flat Panel Detectors) 6a and 6b, a supine bed 7, an upright stand 8, a holding device 9, a DR device 10, an LCD (Liquid Crystal Display) 11, an operation panel 12, and a display lamp 13.

The power supply device 2 includes a power control circuit 21, a main power switch 22, and a power saving control circuit 23. The power control circuit 21 receives power from a commercial power supply or buttery while the main power switch 22 is ON, and supplies the input power to the X-ray high voltage device 3, the cooling device 5, the supine bed 7, the upright stand 8, the holding device 9, the DR device 10, and the like. The power saving control circuit 23 performs processing for implementing power saving concerning the power supplied to each unit by the power control circuit 21. The operation of the power saving control circuit 23 will be described in detail later.

The X-ray high voltage device 3 generates a high voltage based on the power supplied from the power supply device 2, and applies the voltage to the X-ray tube device 4. The X-ray high voltage device 3 may use either a transformer scheme, an inverter scheme, or capacitor scheme.

The X-ray tube device 4 includes an X-ray tube 41 and a temperature sensor 42 which detects the temperature of the X-ray tube 41. The X-ray tube 41 generates X-rays corresponding to the high voltage applied from the X-ray high voltage device 3. As the X-ray tube 41, for example, a rotating anode type X-ray tube can be used. The rotating anode type X-ray tube forms a focal point as an X-ray source on the target surface of a rotating anode target by rotating the rotating anode target using a stator coil and making the electrons emitted from a filament as a cathode collide with the target surface upon accelerating and focusing the electrons.

Note that the X-ray tube 41 is housed in an X-ray tube container filled with a coolant, and is mounted inside the housing of the X-ray tube device 4, together with an irradiation field limiter, which limits the irradiation field of X-rays, and the like.

The X-ray high voltage device 3 includes a stator control circuit 31 and a heating control circuit 32 in addition to a circuit for applying a high voltage to the X-ray tube 41. The stator control circuit 31 adjusts the rotational speed of the above rotating anode target by controlling the amount of current supplied to the stator coil. The heating control circuit 32 adjusts the temperature of the filament by controlling the amount of current supplied to the filament.

The cooling device 5 includes a coolant channel which connects the cooling device 5 to the inside of the housing of the X-ray tube device 4, a radiator connected to the coolant channel, a cooling fan which sends air to the outer surface of the radiator, a pump which circulates the coolant between the housing and the cooling device 5, and a temperature monitoring circuit 51. The radiator performs heat exchange between the coolant and the outside air to cool the coolant heated by the X-ray tube 41. In addition, the cooling fan sends air to promote heat exchange by the radiator. The temperature monitoring circuit 51 suppresses the temperature of the X-ray tube 41 within a predetermined range by monitoring the temperature of the X-ray tube 41 which is detected by the temperature sensor 42 and controlling the rotation speeds of the pump and cooling fan in accordance with the monitored temperature.

The FPDs 6a and 6b each include many X-ray detection elements which are two-dimensionally arrayed. Each X-ray detection element detects the X-rays generated by the X-ray tube 41 and transmitted through an object and outputs an electrical signal. The FPDs 6a and 6b each may be of an indirect conversion type which converts X-rays into fluorescence and then detects it by photoelectric conversion or a direct conversion type which directly converts X-rays into charges. The FPD 6a is used when imaging an object in the supine posture. The FPD 6b is used when imaging the object in the upright posture.

The supine bed 7 includes a top on which an object is placed, a holding mechanism which holds the FPD 6a below the top such that the X-ray detection surface becomes parallel to the placement surface of the top, a moving mechanism which moves the top and the FPD 6a in directions horizontal and perpendicular to the placement surface, operation buttons with which instructions to designate the moving direction and movement amount of the top are input, and a position sensor which detects the positions of the FPD 6a in the vertical and horizontal directions.

The upright stand 8 includes a columnar support standing upright on the mounting surface (floor surface), a holding mechanism which holds the FPD 6b such that the X-ray detection surface of the FPD 6b becomes perpendicular to the mounting surface, a moving mechanism which moves the holding mechanism in the vertical direction, and a position sensor which detects the position of the FPD 6b in the vertical direction.

The holding device 9 holds the X-ray tube device 4. The holding device 9 is suspended from a rail installed on the ceiling of an examination room. The holding device 9 includes an expansion/contraction mechanism which vertically expands/contracts, an operation button with which instructions to move in the horizontal and vertical directions are input, and a horizontal moving mechanism which moves the holding device 9 in the horizontal direction along the rail in accordance with an instruction to move in the horizontal direction which is input via the operation button.

A doctor or technician can adjust the position of the X-ray tube 41 to a position to squarely face the FPD 6a held by the supine bed 7 or the FPD 6b held by the upright stand 8 by making the holding device 9 run along the above rail or extracting/contracting the holding device 9 using the above expansion/contraction mechanism.

The X-ray diagnostic apparatus 1 may have a function of automatically adjusting the position of the X-ray tube 41 in accordance with the position of the FPD 6a or 6b. When imaging an object in the supine posture by using this function, for example, the holding device 9 adjusts the position of the X-ray tube 41 to a position to squarely face the FPD 6a based on the positions of the FPD 6a in the vertical and horizontal directions which are detected by the position sensor of the supine bed 7. In addition, when imaging an object in the upright posture by using this function, for example, the holding device 9 adjusts the position of the X-ray tube 41 to a position to squarely face the FPD 6b based on the position of the FPD 6b in the vertical direction which is detected by the position sensor of the upright stand 8.

The DR device 10 includes a controller 100 constituted by a CPU (Central Processing Unit) and memories such as a ROM (Read Only Memory) and RAM (Random Access Memory) as main components and an auxiliary storage device used to, for example, save medical image data. The controller 100 generates X-ray fluoroscopic image (medical image) data based on output signals from the FPDs 6a and 6b, and saves the generated medical image data in the auxiliary storage device, together with the patient information of an object and the like, in a format complying with the DICOM (Digital Imaging and Communication in Medicine) standard. The controller 100 sometimes transmits generated medical image data to a host system such as a PACS (Picture Archiving and Communication System) system.

The DR device 10 includes a power control circuit 101 which supplies power to the devices connected to the DR device 10. In this embodiment, the FPDs 6a and 6b, the LCD 11, and the operation panel 12 are connected to the DR device 10. The power control circuit 101 supplies the power, supplied from the power supply device 2 to the DR device 10, to the FPDs 6a and 6b, the LCD 11, and the operation panel 12.

The LCD 11 displays, for example, the medical images based on medical image data generated by the DR device 10. The operation panel 12 includes a mouse, keyboard, trackball, touch panel, and various types of buttons. The operation panel 12 is used to, for example, input the patient information (the patient ID, name, sex, and the like) of an object, designate an examination region (imaging region) of the object, and input an examination start instruction.

The power saving control circuit 23 of the power supply device 2 includes a processor which performs various types of arithmetic operations, memories such as a ROM and a RAM, and other ICs. The display lamp 13, an illumination system 200 in the examination room, and a human sensor 201 which detects the presence of a person in the examination room are connected to the power saving control circuit 23. The display lamp 13 is formed from, for example, one or a plurality of LEDs. The power saving control circuit 23 turns on or off or blinks the display lamp 13. The illumination system 200 includes, for example, an illumination such as a fluorescent lamp or LED which is turned on/off in accordance with the operation of an illumination switch provided in the examination room. The human sensor 201 is a reflective sensor which detects a moving object in the examination room by using, for example, infrared light.

The power saving control circuit 23 performs processing for power saving on the X-ray diagnostic apparatus 1. For example, the power saving control circuit 23 switches the operation modes of the X-ray high voltage device 3, the cooling device 5, the FPDs 6a and 6b, the supine bed 7, the upright stand 8, the holding device 9, the DR device 10, the LCD 11, and the operation panel 12 between the normal mode and the power saving mode. The X-ray high voltage device 3, the cooling device 5, the FPDs 6a and 6b, the supine bed 7, the upright stand 8, the holding device 9, the DR device 10, the LCD 11, and the operation panel 12 will be referred to as control target devices hereinafter.

In this case, the normal mode is a mode of making each control target device operate with its intrinsic performance.

The power saving mode is a mode of making each control target device operate with a lower consumption of power supplied from the power control circuit 21 than in the normal mode or stopping the operation.

[Setting Information Concerning Power Saving Mode]

The memory of the power saving control circuit 23 stores setting information 230 which defines conditions for transition to the power saving mode for each control target device and methods of implementing the power saving mode. The power saving control circuit 23 repeatedly determines the success or failure of each transition condition defined by the setting information 230. If a given transition condition holds, the power saving control circuit 23 causes the control target device for which the transition condition holds to transition to the power saving mode by the implementation method defined by the setting information 230 in correspondence with the transition condition.

Combinations of the transition conditions and the implementation methods defined by the setting information 230 will be described with reference to FIG. 2. As indicated on the left side of FIG. 2, as conditions for transition to the power saving mode, for example, conditions (a) to (g) can be used:

(a) "no operation for predetermined time"

An "operation" is, for example, the operation of the operation panel 12. Note however that this "operation" may be the operation of an operation unit of each control target device. Assume that if there is no operation on a certain control target device for a predetermined period of time, it is assumed that there is low possibility that the device will be used thereafter. In this case, this condition may be used to cause the device to transition to the power saving mode.

(b) "any examination program being selected"

An "examination program" is a computer program which defines a sequence for controlling each device of the X-ray diagnostic apparatus 1 when imaging an examination region as a target and processing for generating medical image data based on the data obtained by imaging. An "examination program" is, for example, a program for supine imaging of an object on the supine bed 7 or a program for upright imaging of an object on the upright stand 8. Depending on the examination program to be used, some control target device is not used for imaging. When causing such a control target device to transition to the power saving mode, this condition may be used.

(c) "processing other than processing from start of examination to end of examination being executed"

Assume that "processing from start of examination to end of examination" is processing from the time point at which, for example, an instruction to start an examination on an object is input by the operation of the operation panel 12 to the time point at which the storage of the medical image data generated by imaging is complete. "Processing other than processing from start of examination to end of examination" includes, for example, a post process such as checking the image obtained by imaging an object and processing associated with a setting change in the X-ray diagnostic apparatus 1. At the time of the execution of such processing, there is low possibility that, for example, the FPDs 6a and 6b, the supine bed 7, the upright stand 8, and the holding device 9 will be used. When, therefore, causing these control target devices to transition to the power saving mode, this condition may be used.

(d) "examination room not being used"

This transition condition holds when, for example, an illumination included in the illumination system 200 in the examination room is OFF or no moving object (person) is detected by the human sensor 201. If the examination room is not used, it is assumed that the X-ray diagnostic apparatus 1 is not used either. When causing a control target device to transition to the power saving mode under this circumstance, this condition may be used.

(e) "set time having arrived"

A "set time" is, for example, a time zone in which it is clear that no examination will be performed, such as a lunch break. When causing a control target device to transition to the power saving mode in such a time zone, this condition may be used.

(f) "DR device being shut down"

The DR device 10 is shut down under the control of the controller 100 when, for example, the operator operates the operation panel 12 to issue an instruction to shut down. When the DR device 10 is shut down, there is low possibility that other control target devices will be used. When, therefore, causing these control target devices to transition to the power saving mode, this condition may be used.

(g) "temperature of X-ray tube being less than threshold"

A "threshold" may be set to, for example, the upper limit of the temperatures at which there is no need for cooling by the cooling device 5. That is, this transition condition is mainly aimed at the cooling device 5. When suppressing the power consumption of the cooling device 5, this condition may be used.

It is possible to set various transition conditions other than these conditions (a) to (g). A transition condition for one control target device may be formed by combining a plurality conditions of the conditions (a) to (g) and other conditions.

As indicated on the right side of FIG. 2, as power saving implementation methods, for example, methods (i) to (ix) given below can be used:

(i) concerning the X-ray high voltage device 3, "turning off stator output" or "lowering temperature of heated filament"

"Turning off stator output" indicates stopping the supply of a current from the stator control circuit 31 to the stator coil of the X-ray tube 41. "Lowering temperature of heated filament" indicates lowering the target temperature of the heated filament by the heating control circuit 32.

(ii) concerning the cooling device 5, "intermittent driving", "flow rate adjustment", or "stopping"

"Intermittent driving" is a driving method of providing periodic break periods in the operation of the pump or cooling fan of the cooling device 5. "Flow rate adjustment" indicates decreasing the flow rate of coolant to be circulated between the X-ray tube device and the cooling device 5. "Stopping" indicates stopping the pump or cooling fan.

(iii) to (vi) concerning the FPDs 6a and 6b, the supine bed 7, the upright stand 8, and the holding device 9, "turning off power"

"Turning off power" in this case indicates individually stopping the supply of power to the FPDs 6a and 6b, the supine bed 7, the upright stand 8, and the holding device 9.

(vii) concerning the DR device 10, "standing by" or "shutting down"

"Standing by" indicates the processing of saving an operation state in the memory of the controller 100 and turning off the power of the devices of the DR device 10 except for the memory. "Shutting down" indicates the processing of finishing the operating system of the DR device 10 and turning off the power of each device included in the DR device 10.

(viii) concerning the LCD 11, "turning off power" or "switching off backlight"

"Turning off power" in this case indicates stopping the supply of power to the LCD 11. "Switching off backlight" indicates switching off the backlight without stopping the supply of power to the LCD 11.

(ix) concerning the whole system (all the devices of the X-ray diagnostic apparatus 1), "turning off power"

"Turning off power" in this case indicates switching off the main power switch 22.

It is possible to implement the power saving mode of each device by various methods other than the methods (i) to (ix) described above.

It is possible to change, on the user side, the transition conditions and implementation methods defined by the setting information 230. For example, the DR device 10 executes the processing associated with this change. Alternatively, a computer for setting may be connected to the power supply device 2 to make the computer execute the processing associated with the change.

Specific examples of the processing associated with power saving control will be described next.

Specific Example 1

In this example, the power saving control circuit 23 executes the processing associated with power saving with respect to the supine bed 7, the upright stand 8, the holding device 9, and the DR device 10 as control target devices. Assume that the setting information 230 has defined transition conditions for each control target device by combining the conditions (a), (b), (c), and (f) and the like described above.

FIG. 3 is a flowchart for explaining the operation of the X-ray diagnostic apparatus 1 in this example.

The operation indicated by this flowchart is started when the main power switch 22 is turned on.

When the main power switch 22 is turned on, the power control circuit 21 starts supplying power to the respective devices including the supine bed 7, the upright stand 8, the holding device 9, and the DR device 10. When the supply of power is started, the respective devices included in the X-ray diagnostic apparatus 1 are activated (step S101).

When the activation is complete, the X-ray diagnostic apparatus 1 performs a self-check for detecting an abnormality (step S102). A self-check is performed by causing the processor of each device to execute a program for the self-check. A given device may perform a self-check on another device in addition to a self-check on itself. For example, the controller 100 of the DR device 10 can also perform self-checks on the LCD 11, the operation panel 12, and the FPDs 6a and 6b connected to the DR device 10. Each device gives a warning by a display or audio output operation when a self-check result indicates an abnormality. In addition, one of the respective devices, for example, the DR device 10 may collect self-check results, and a warning against an abnormality may be given under the control of the controller 100 of the DR device 10.

Such self-checks must always be executed when starting to use the X-ray diagnostic apparatus 1, from the viewpoint of ensuring safety for an object. In other words, at least when the X-ray diagnostic apparatus 1 is activated, it is necessary to activate the respective devices included in the X-ray diagnostic apparatus 1 by supplying power to the devices.

When the self-check is complete, each device transitions to a state in which it waits for an instruction from the operator or another device. If any instruction is received, each device operates in accordance with the instruction.

An operation of the DR device 10 will be described as an example.

The DR device 10 transitions to a state in which it waits for an instruction to start an examination after the self-check. When an instruction to start an examination is issued by the operation of the operation panel 12, the controller 100 of the DR device 10 operates in accordance with the flowchart of FIG. 4.

First of all, the controller 100 accepts an input of patient information of an object as an examination target (step S201). The operator inputs patient information by, for example, operating the operation panel 12. A host system such as an HIS (Hospital Information System) or RIS (Radiology Information System) connected to the X-ray diagnostic apparatus 1 may input patient information to the X-ray diagnostic apparatus 1.

After the patient information is input, the controller 100 accepts the designation of an examination region (imaging region) of the object (step S202). The operator designates an examination region from candidates such as the head region, chest region, abdominal region, arm region, and leg region by, for example, operating the operation panel 12.

After an examination region is designated, the controller 100 selects an examination program for imaging the examination region (step S203). An examination program is prepared for, for example, each examination region. Examination programs as candidates to be selected in step S203 can be roughly classified into the first program for imaging an object in the supine posture and the second program for imaging an object in the upright posture.

After an examination program is decided, the controller 100 decides imaging conditions such as a tube voltage and a tube current based on the examination program and the patient information input in step S201 (step S204). Thereafter, the controller 100 waits for the input of an imaging start instruction by the operator (step S205).

During this period, the operator makes setting to make the patient as the object, the X-ray tube 41, and the FPDs 6a and 6b have a positional relationship suitable for imaging. For example, if an examination region requires imaging in the supine posture, the operator lays the patient as the object on the supine bed 7, and adjusts the height and horizontal position of the top of the supine bed 7 and the position of the X-ray tube device 4 to set a proper positional relationship between the FPD 6a and the X-ray tube device 4 held by the holding device 9. Alternatively, if an examination region requires imaging in the upright posture, the operator stands the patient as the object at a predetermined position near the upright stand 8 and adjusts the height of the FPD 6b held by the upright stand 8 and the position of the X-ray tube device 4 so as to set a proper positional relationship between the FPD 6b and the X-ray tube device 4 held by the holding device 9.

When the setting is complete, the operator operates the operation panel 12 to issue an instruction to start imaging. If this instruction is issued (YES in step S205), the controller 100 performs X-ray imaging of the object (step S206). More specifically, the controller 100 causes the X-ray tube 41 to generate X-rays by supplying a high voltage from the X-ray high voltage device 3 to the X-ray tube 41 in accordance with the sequence set by the examination program selected in step S203 and the imaging conditions decided in step S204. Subsequently, if the examination program selected in step S203 is the first program, the controller 100 captures, in the DR device 10, the data generated by causing the FPD 6a to detect X-rays transmitted through the object. If the examination program selected in step S203 is the second program, the controller 100 captures, in the DR device 10, the data generated by causing the FPD 6b to detect X-rays transmitted through the object.

After X-ray imaging, the controller 100 generates medical image data by performing the processing set by the examination program selected in step S203 with respect to the data captured from the FPD 6a or 6b (step S207). In addition, the controller 100 saves the generated medical image data (step S208). The save destination of medical image data may be an auxiliary storage device of the DR device 10 or a host system such as a PACS.

Figure 4:
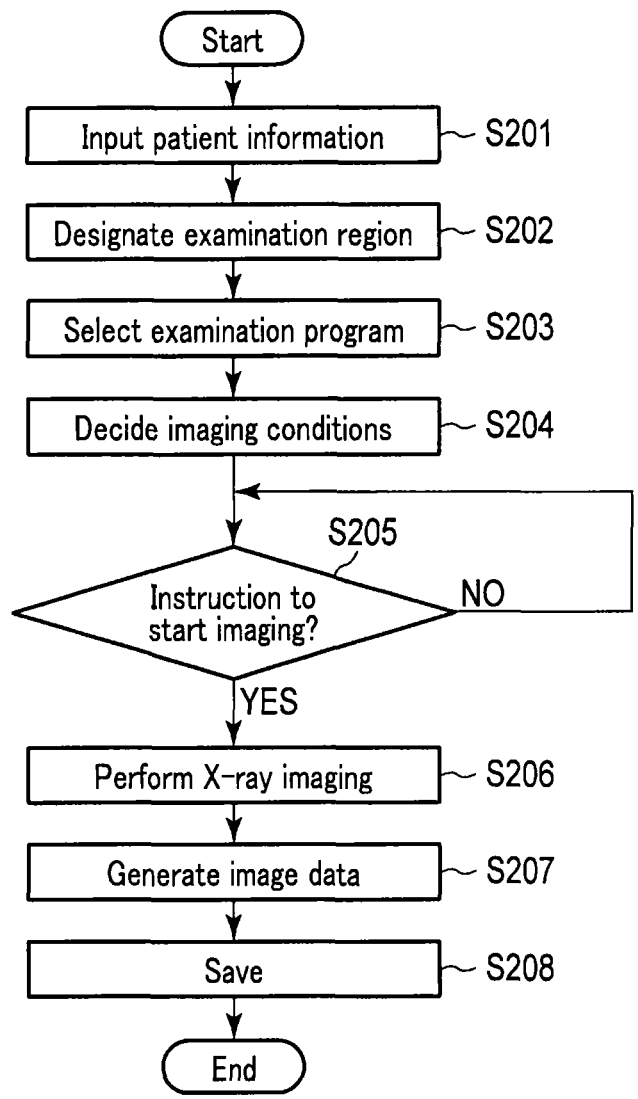
FIG. 4 is a flowchart for explaining the operation of a DR device in Specific Example 1.

With step S208, the operation indicated by the flowchart of FIG. 4 is complete. After the examination following such a procedure, the controller 100 performs a post-process such as displaying the medical image data saved in step S208 on the LCD 11. As is obvious from the description of the flowchart, the controller 100 functions as a selection unit which selects an examination program for controlling a plurality of devices of the X-ray diagnostic apparatus 1 from a plurality of examination programs, when obtaining a medical image and also functions as an imaging control unit which obtains a medical image by controlling the above plurality of devices in accordance with the program selected by the selection unit.

Return to the description of the flowchart of FIG. 3. In Specific Example 1, after step S102, the power saving control circuit 23 operates in accordance with steps S103 to S115.

That is, first of all, the power saving control circuit 23 determines whether an examination on an object is being executed (step S103). If the DR device 10 is operating in accordance with the flowchart of FIG. 4, the power saving control circuit 23 determines that an examination is being executed (YES in step S103). In this case, the power saving control circuit 23 determines whether the examination program selected in step S203 is the first or second program (step S104).

If the power saving control circuit 23 determines that the examination program selected in step S203 is the first program ("supine" in step S104), the upright stand 8 is not used in this examination. For this reason, the power saving control circuit 23 causes the upright stand 8 to transition to the power saving mode (step S105). If, for example, "turning off power" is defined as a power saving implementation method for the upright stand 8 by the setting information 230, the power saving control circuit 23 outputs, to the power control circuit 21, an instruction to cause the upright stand 8 to transition to the power saving mode in step S105. Upon receiving this instruction, the power control circuit 21 stops the supply of power to the upright stand 8.

Following step S105, if there is a device, of the control target devices in this specific example except for the upright stand 8, which has been in the power saving mode, the power saving control circuit 23 cancels the power saving mode of the device and causes it to return to the normal mode (step S106). If, for example, there is a control target device to which the supply of power is being stopped, the power saving control circuit 23 outputs an instruction to the power control circuit 21 to resume the supply of power. When this instruction is input, the power control circuit 21 resumes the supply of power to the device.

On the other hand, if the power saving control circuit 23 determines that the examination program selected in step S203 is the second program ("upright" in step S104), the supine bed 7 is not used in the examination. For this reason, the power saving control circuit 23 causes the supine bed 7 to transition to the power saving mode (step S107). If, for example, "turning off power" is defined as a power saving implementation method for the supine bed 7 by the setting information 230, the power saving control circuit 23 outputs, to the power control circuit 21, an instruction to cause the supine bed 7 to transition to the power saving mode in step S107. Upon receiving this instruction, the power control circuit 21 stops the supply of power to the supine bed 7.

Following step S107, if there is a device, of the control target devices in this specific example except for the supine bed 7, which has been in the power saving mode, the power saving control circuit 23 cancels the power saving mode of the device and causes it to return to the normal mode as in step S106 (step S108).

After step S106 or S108, the operation of the power saving control circuit 23 returns to step S103.

In step S103, if the DR device 10 is not operating in accordance with the flowchart of FIG. 4, the power saving control circuit 23 determines that an examination on the object is not being executed (NO in step S103). In this case, the power saving control circuit 23 determines whether the DR device 10 is executing a post-process (step S109).

If the DR device 10 is executing a post-process, it is assumed that the control target devices in this specific example except for the DR device 10 are not used. For this reason, upon determining in step S109 that a post-process is being executed (YES in step S109), the power saving control circuit 23 causes the control target devices except for the DR device 10, i.e., the supine bed 7, the upright stand 8, and the holding device 9 to transition to the power saving mode (step S110). If, for example, "turning off power" is defined as a power saving implementation method for the supine bed 7, the upright stand 8, and the holding device 9 by the setting information 230, the power saving control circuit 23 outputs, to the power control circuit 21, an instruction to cause the supine bed 7, the upright stand 8, and the holding device 9 to transition to the power saving mode in step S110. Upon receiving this instruction, the power control circuit 21 stops the supply of power to the supine bed 7, the upright stand 8, and the holding device 9. After step S110, the operation of the power saving control circuit 23 returns to step S103.

Upon determining in step S109 that a post-process is not being executed (NO in step S109), the power saving control circuit 23 determines whether the DR device 10 is shut down (step S111). For example, when the operator operates the operation panel 12 to input an instruction to shut down, the DR device 10 is shut down under the control of the controller 100.

It is assumed that while the DR device 10 is shut down, the X-ray diagnostic apparatus 1 is not used in an examination or the like. For this reason, upon determining in step S111 that the DR device 10 is shut down (YES in step S111), the power saving control circuit 23 turns off the main power switch 22 (step S112). When the main power switch 22 is turned off, the power control circuit 21 stops the supply of power to each device included in the X-ray diagnostic apparatus 1.

When step S112 is executed, the operation indicated by the flowchart of FIG. 3 is complete.

On the other hand, upon determining in step S111 that the DR device 10 is not shut down (NO in step S111), the power saving control circuit 23 determines whether no operation has been performed on each control target device for a predetermined time or more (step S113). This determination is performed by, for example, using the timer of the power saving control circuit 23. That is, the power saving control circuit 23 monitors an operation on each control target device, and measures the elapsed time since the last operation on any of the control target devices by using the timer. The power saving control circuit 23 performs the determination in step S113 by comparing the time measured by the timer with a predetermined time set in advance.

Upon determining that no operation has been performed on each control target device for the predetermined time or more (YES in step S113), the power saving control circuit 23 causes all the control target devices to transition to the power saving mode (step S114). In step S114, the power saving control circuit 23 causes the supine bed 7, the upright stand 8, and the holding device 9 to transition to the power saving mode by the same method as that in step S110. In addition, the power saving control circuit 23 commands the DR device 10 to stand by. When the DR device 10 receives this command, the controller 100 of the DR device 10 causes the DR device 10 to transition to the standby state. Note that the operator operates the operation panel 12 in the standby state of the DR device 10, the operation panel 12 outputs an interrupt signal to the controller 100. Upon receiving this interrupt signal, the controller 100 cancels the standby state and causes the DR device 10 to return to the normal mode.

Upon determining that an operation has been performed on each control target device within the predetermined time (NO in step S113), the power saving control circuit 23 cancels the power saving mode of all the control target devices which have been in the power saving mode, and causes them to return to the normal mode (step S115).

After steps S114 or S115, the operation of the power saving control circuit 23 returns to step S103.

Specific Example 2

Specific Example 2 will be described next.

In this example, the power saving control circuit 23 executes the processing associated with power saving with respect to the cooling device 5 as a control target device. Assume that the setting information 230 has defined transition conditions for the cooling device 5 by combining the above conditions (c), (f), and (g) and the like described above.

Figure 5:
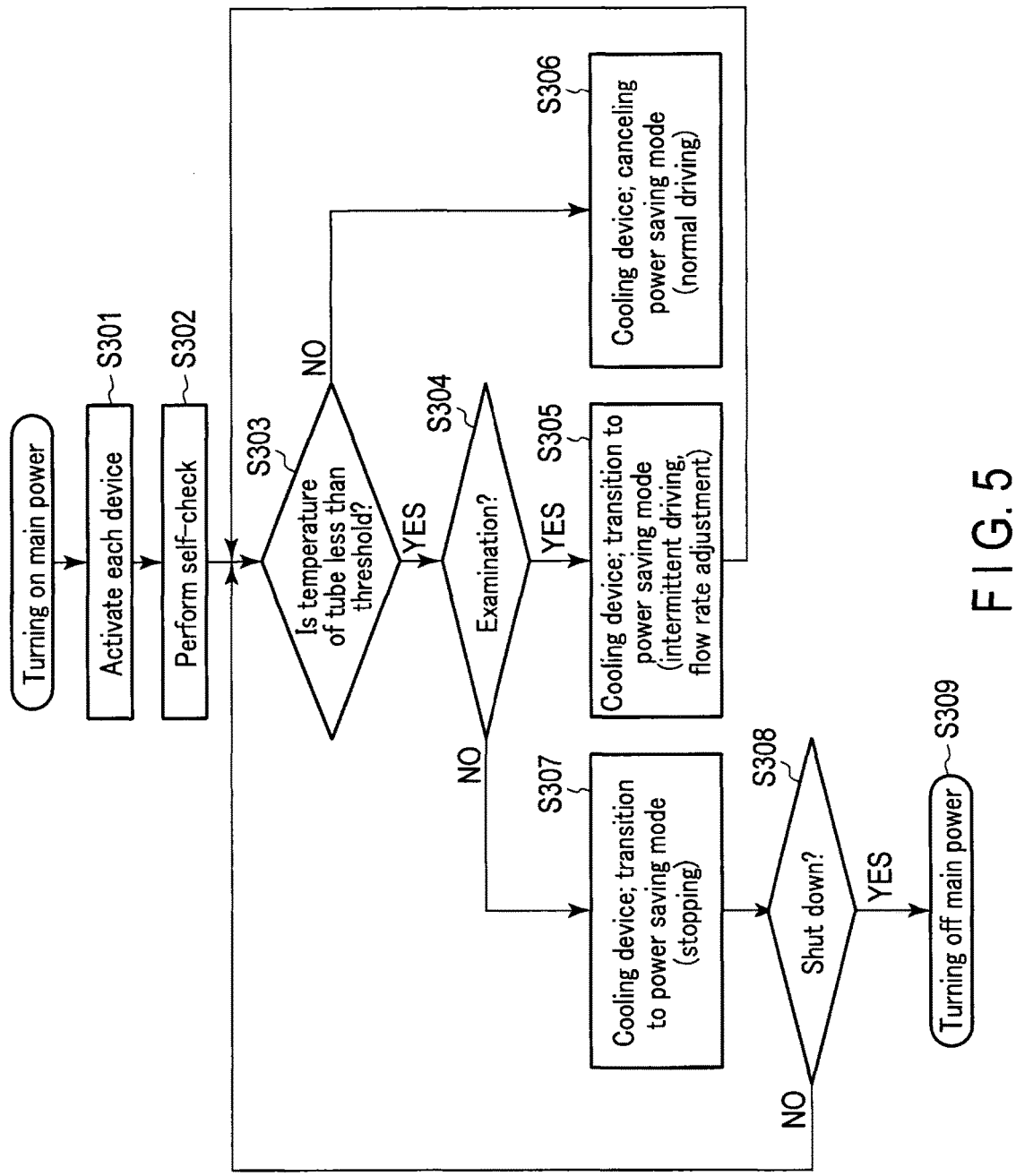
FIG. 5 is a flowchart for explaining the operation of the X-ray diagnostic apparatus in Specific Example 2.

FIG. 5 is a flowchart for explaining the operation of the X-ray diagnostic apparatus 1 in this example.

The operation indicated by this flowchart is started when the main power switch 22 is turned on.

When the main power switch 22 is turned on, the power control circuit 21 starts supplying power to the respective devices including the cooling device 5. When the supply of power is started, the respective devices included in the X-ray diagnostic apparatus 1 are activated (step S301).

When the activation is complete, the X-ray diagnostic apparatus 1 performs a self-check as in step S202 in Specific Example 1 (step S302). When the self-check is complete, each device transitions to a state in which it waits for an instruction from the operator or another device. If any instruction is received, each device operates in accordance with the instruction. For example, the DR device 10 operates in accordance with the flowchart of FIG. 4 as described in Specific Example 1.

After step S302, the power saving control circuit 23 operates in accordance with steps S303 to S309.

That is, first of all, the power saving control circuit 23 determines whether the temperature of the X-ray tube 41 which is detected by the temperature sensor 42 is less than a predetermined threshold (step S303). This threshold is, for example, the upper limit of the temperatures at which there is no need for cooling by the cooling device 5.

If the temperature of the X-ray tube 41 is less than the threshold (YES in step S303), the power saving control circuit 23 determines whether any examination on the object is being executed (step S304). If the DR device 10 is operating in accordance with the flowchart of FIG. 4, the power saving control circuit 23 determines that an examination is being executed (YES in step S304). In this case, the temperature of the X-ray tube 41 is currently low enough to require no cooling, although there may be a temperature rise during the examination. For this reason, the power saving control circuit 23 causes the cooling device 5 to transition to the power saving mode (step S305). If, for example, "intermittent driving" is defined as a power saving implementation method for the cooling device 5, the power saving control circuit 23 issues an instruction to intermittently drive to the cooling device 5. Upon receiving this instruction, the cooling device 5 intermittently drives the pump or cooling fan. If "flow rate adjustment" is defined as a power saving implementation method for the cooling device 5, the power saving control circuit 23 issues an instruction to the cooling device 5 to decrease the flow rate of coolant to be circulated between the X-ray tube device 4 and the cooling device 5. Upon receiving this instruction, the cooling device 5 decreases the flow rate of coolant by decreasing the number of revolutions of the pump to the number of revolutions lower than that in the normal mode.

If the power saving control circuit 23 determines in step S303 that the temperature of the X-ray tube 41 is equal to or more than the threshold (NO in step S303), the X-ray tube 41 needs to be cooled. For this reason, the power saving control circuit 23 cancels the power saving mode of the cooling device 5, if it is in the power saving mode, through step S305 or S307, and causes the cooling device 5 to return to the normal mode (step S306).

After step S305 or S306, the operation of the power saving control circuit 23 returns to step S303.

If the DR device 10 is not operating in accordance with the flowchart of FIG. 4, the power saving control circuit 23 determines in step S304 that no examination on the object is being executed (NO in step S304). In this case as well, the power saving control circuit 23 causes the cooling device 5 to transition to the power saving mode (step S307). In step S307, however, the power saving control circuit 23 issues an instruction to the power control circuit 21 to stop the supply of power to the cooling device 5. Upon receiving this instruction, the power control circuit 21 completely stops the supply of power to the cooling device 5 (turning off power).

After step S307, the power saving control circuit 23 determines whether the DR device 10 is shut down (step S308). Upon determining that the DR device 10 is shut down (YES in step S308), the power saving control circuit 23 turns off the main power switch 22 as in step S112 in Specific Example 1 (step S309). When the main power switch 22 is turned off, the power control circuit 21 stops the supply of power to each device included in the X-ray diagnostic apparatus 1. When step S309 is executed, the operation indicated by the flowchart of FIG. 5 is complete.

Upon determining in step S308 that the DR device 10 is not shut down (NO in step S308), the operation of the power saving control circuit 23 returns to step S303.

[Notification of Operation Mode]

The power saving control circuit 23 executes the processing for notifying the operation mode of a control target device by using the display lamp 13 concurrently with the operation in steps S103 to S115 in Specific Example 1 or the operation in steps S303 to S309 in Specific Example 2.

For example, the power saving control circuit 23 causes the display lamp 13 to illuminate in the first color (e.g., green) while all the control target devices are operating in the normal mode, and causes the display lamp 13 to illuminate in the second color (e.g., red) while at least one of the control target devices is in the power saving mode.

It is possible to notify the operation mode of each control target device by using the display lamp 13.

In this case, for example, the display lamp 13 is provided for each control target device. The power saving control circuit 23 causes the display lamp 13 corresponding to a control target device operating in the normal mode to illuminate in the first color, and causes the display lamp 13 corresponding to a control target device operating in the power saving mode to illuminate in the second color.

As described above, according to this embodiment, the power saving control circuit 23 causes each control target device to transition to the power saving mode at a proper timing. It is therefore possible to suppress unnecessary power consumption by the X-ray diagnostic apparatus 1.

In addition, the power saving control circuit 23 causes a control target device in the power saving mode to transition to the normal mode, when the corresponding transition condition becomes false. Canceling the power saving mode of each device in this manner without going through the operation of the operator can quickly start an examination using the X-ray diagnostic apparatus 1.

In addition, the power saving control circuit 23 notifies the current operation mode of each control target device by using the display lamp 13. This allows the operator to easily grasp the presence/absence of a device which has transitioned to the power saving mode.

Specific Example 3

Figure 6:
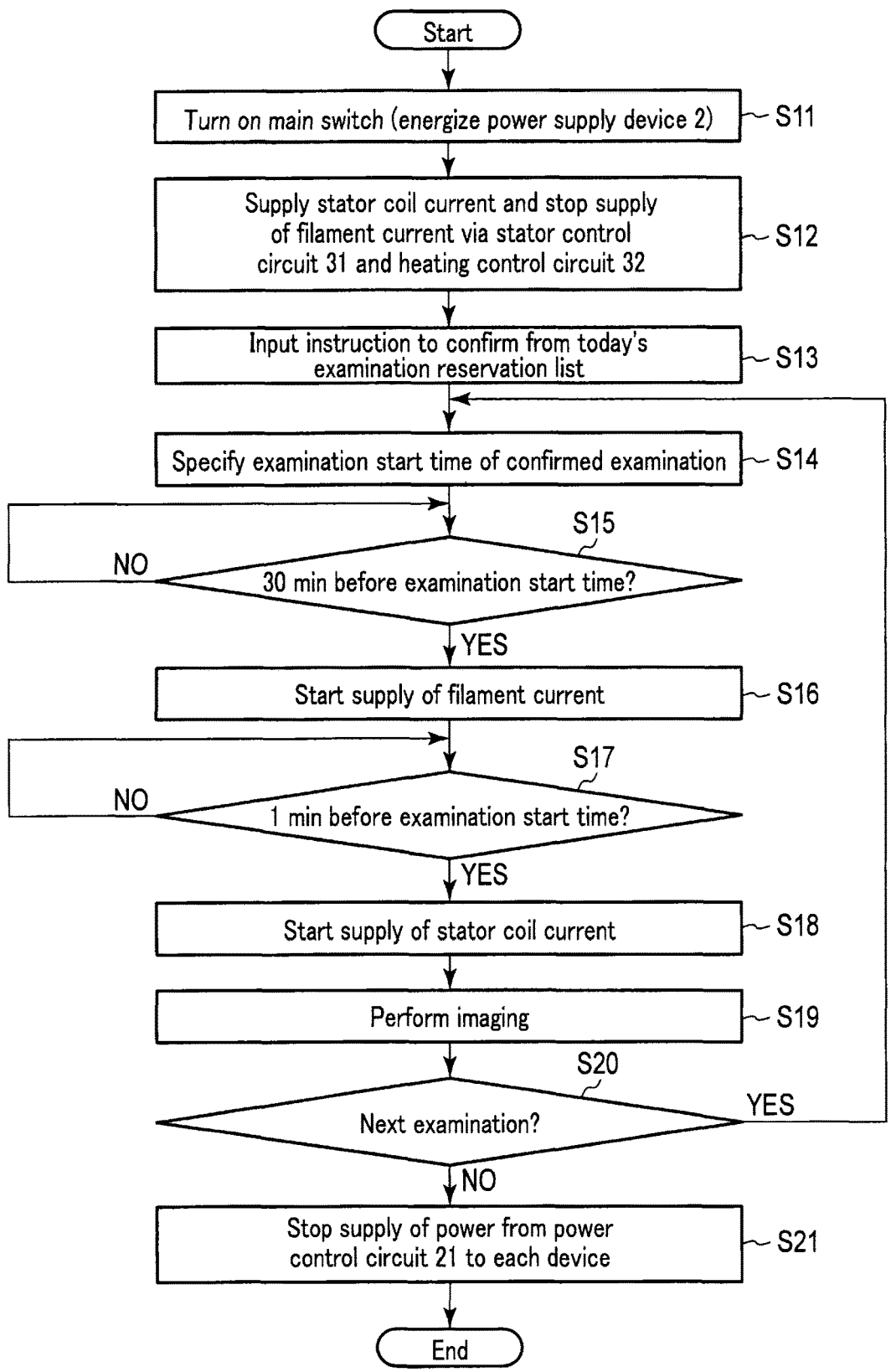
FIG. 6 is a flowchart for explaining the operation of the X-ray diagnostic apparatus in Specific Example 3.

FIG. 6 shows a processing procedure in Specific Example 3. For example, at the start of every morning, the main power switch 22 of the system is switched from OFF to ON (step S11). At this time, the power control circuit 21 and the power saving control circuit 23 of the power supply device 2 are energized. The power saving control circuit 23 controls the stator control circuit 31 and the heating control circuit 32 of the X-ray high voltage device 3. This control stops the supply of a current from the stator control circuit 31 to the stator coil of the rotating anode of the X-ray tube device 4, and also stops the supply of a current from the heating control circuit 32 to the cathode filament of the X-ray tube device 4 (step S12).

The imaging technician then operates the operation panel 12 to confirm at least one examination on the today's examination reservation list displayed on the LCD 11 (step S13). The power saving control circuit 23 specifies an examination start time from examination information concerning the next confirmed examination (step S14).

The power saving control circuit 23 repeatedly determines whether the current time has reached the time 30 min before (the first time) the examination start time (step S15). When the current time has reached the time 30 min before the examination start time, the power saving control circuit 23 controls the heating control circuit 32 to start the supply of a current from the heating control circuit 32 to the cathode filament of the X-ray tube device 4 (step S16). This starts to heat the cathode filament to guarantee the emission of a sufficient amount of thermos-electrons at the examination start time.

Subsequently, the power saving control circuit 23 repeatedly determines whether the current time has reached, for example, the time 1 min (the second time) before the examination start time (step S17). When the current time has reached the time 1 min before the examination start time, the power saving control circuit 23 controls the stator control circuit 31 to start the supply of a current from the stator control circuit 31 to the stator coil of the rotating anode of the X-ray tube device 4 (step S18). With this control, the rotating anode starts rotating, and the rotation of the rotating anode will reach a steady state at the examination start time.

When imaging (examination) is finished (step S19), the power saving control circuit 23 controls the stator control circuit 31 and the heating control circuit 32 of the X-ray high voltage device 3 to stop the supply of a current from the stator control circuit 31 to the stator coil of the rotating anode of the X-ray tube device 4 and stop the supply of a current from the heating control circuit 32 to the cathode filament of the X-ray tube device 4. The power saving control circuit 23 determines the presence/absence of the next examination (step S20). If there is no next examination, the power saving control circuit 23 stops the supply of a current from the power control circuit 21 to the respective devices 3 and 5 to 10 (step S21). If there is the next examination, the process returns to step S14 to execute the processing in steps S14 to S21.

Note that the supply of a current from the heating control circuit 32 to the cathode filament of the X-ray tube device 4 may be stopped/started so as to maintain the supply of a current to the cathode filament and control the magnitude of the current value. When a low current is supplied to the cathode filament, the cathode filament is maintained at a predetermined temperature. When a high current is supplied to the cathode filament, the cathode filament is heated to a sufficient temperature for the emission of a predetermined amount of thermo-electrons.

In addition, a method simpler than the control method described above may be used. For example, the supply/stop of a current to the stator coil and the cathode filament may be switched in accordance with a predetermined time schedule when the main power switch 22 is switched from OFF to ON. For example, the supply of a current to the stator coil and the cathode filament is started at 8:30 every morning, the supply of a current to the stator coil and the cathode filament is stopped in the time zone from 12:00 to 13:00 every day, and the supply of a current to the stator coil and the cathode filament is stopped at 17:00 every day regardless of, for example, the time when the main power switch 22 is switched from OFF to ON and the examination start time.

In addition, when the DR device 10 is shut down, the power saving control circuit 23 stops the supply of a current to the stator coil and the cathode filament, because no X-rays can be applied.

Furthermore, when no operation is performed via the operation panel 12 for a predetermined time, the power saving control circuit 23 determines that no examination is performed, and stops the supply of a current to the stator coil and the cathode filament.

In addition, the power saving control circuit 23 stops the supply of a current to the stator coil during a period other than a period from the instant 1 min before the examination start time to the end of the examination.

Furthermore, the power saving control circuit 23 stops the supply of a current to the stator coil when the illumination system 200 in the examination room is turned off, and no person is detected by the human sensor 201 in the examination room.

Specific Example 4

Figure 7:
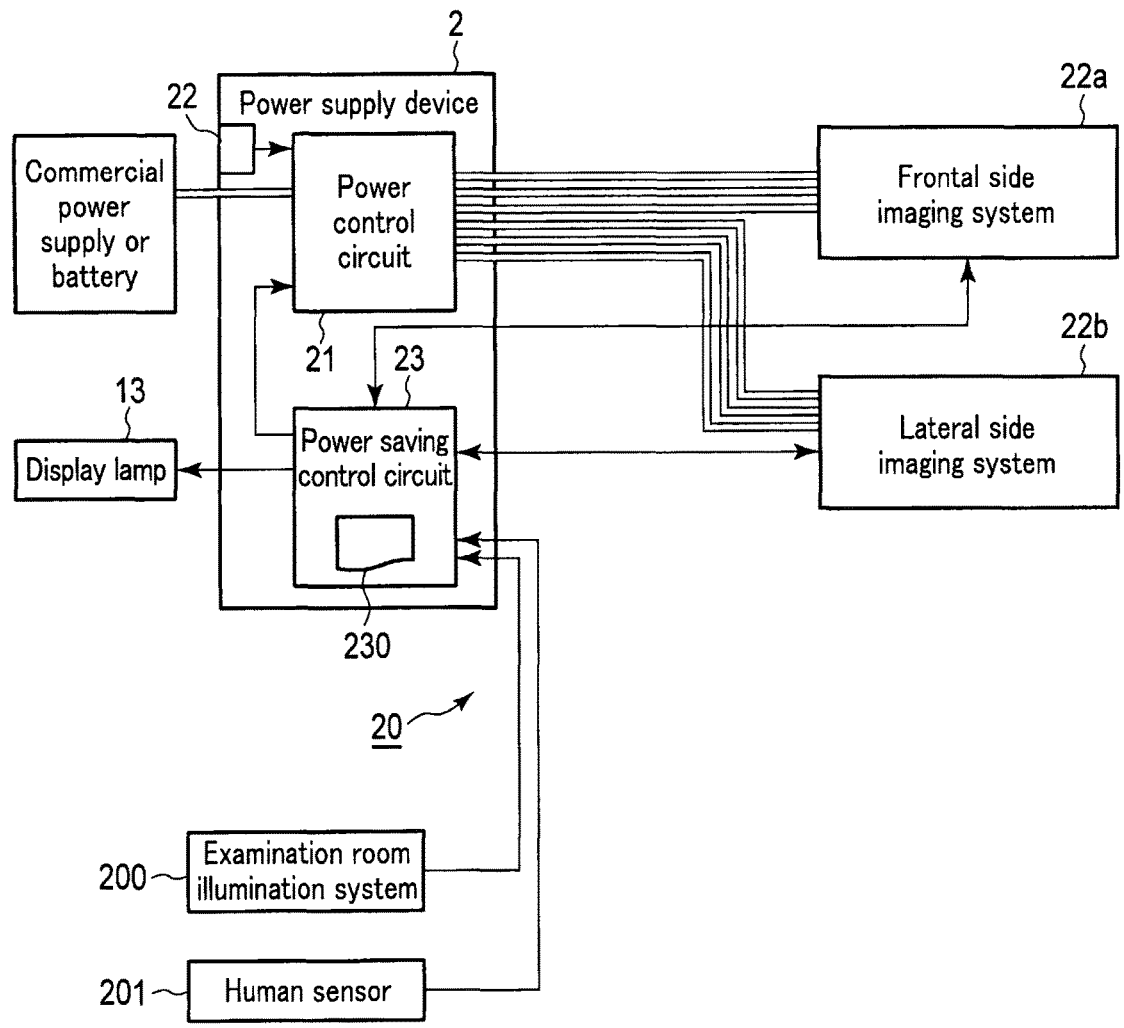
FIG. 7 is a block diagram showing the arrangement of the main part of the X-ray diagnostic apparatus according to Specific Example 4.

FIG. 7 shows power lines of a biplane type X-ray diagnostic apparatus corresponding to Specific Example 4. The biplane type X-ray diagnostic apparatus effective for a circulatory system examination or surgical operation includes two imaging systems, namely, a frontal side imaging system 21 and a lateral side imaging system 22. The power control circuit 21 is heavily currently connected to the frontal side imaging system 21 and the lateral side imaging system 22 via separate power lines, i.e., independent power lines. This allows the power control circuit 21 to separately manage the stop/start of the supply of power to the frontal side imaging system 21 and the lateral side imaging system 22. Conventionally, the power control circuit is connected to the frontal side imaging system 21 and the lateral side imaging system 22 via a common power line, and hence it is not possible to separately manage the stop/start of the supply of power.

The power saving control circuit 23 inputs examination program data, and controls the power control circuit 21 to stop the supply of power itself to a system which is not used when performing an examination other than an examination using both the frontal side imaging system 21 and the lateral side imaging system 22, i.e., an examination using only one of the frontal side imaging system 21 and the lateral side imaging system 22 without using the other.

Modification

The arrangement disclosed in the above embodiment can be modified into various forms.

For example, the above embodiment has exemplified the X-ray diagnostic apparatus 1 as an example of a medical imaging apparatus. However, the control concerning power saving disclosed in the above embodiment may be applied to other types of medical imaging apparatuses, e.g., an X-ray CT apparatus, MRI apparatus, and ultrasonic diagnostic apparatus.

In addition, the control concerning power saving disclosed in the above embodiment may be applied to X-ray diagnostic apparatuses other than the general imaging system. X-ray diagnostic apparatuses other than the general imaging system include, for example, an X-ray fluoroscopy apparatus which holds an X-ray source and an X-ray detector on a C-arm Ω-arm and displays the image obtained by imaging in real time while obtaining an X-ray fluoroscopic image of an object laid on a bed at a predetermined frame rate.

In addition, when such an X-ray fluoroscopy apparatus and the general imaging system are arranged in the same examination room, the control concerning power saving disclosed in the above embodiment may be applied to the system including both the apparatuses. Assume that in this case, the selection of an examination program like the condition (b) described above is used as a transition condition. In this case, various implementation forms can be used. For example, if an examination program using the general imaging system is selected, each device of the X-ray fluoroscopy apparatus is caused to transition to the power saving mode, whereas if an examination program using the X-ray fluoroscopy apparatus is selected, each device of the general imaging system is caused to transition to the power saving mode.

In addition, Specific Examples 1 and 2 have exemplified the cases in which some of the plurality of devices of the X-ray diagnostic apparatus 1 are caused to transition to the power saving mode. However, when, for example, the transition condition (d) or (e) described above holds, all the devices of the X-ray diagnostic apparatus 1 may be caused to transition to the power saving mode.

Furthermore, Specific Example 1 has exemplified the case in which when the first program is selected, the upright stand 8 is caused to transition to the power saving mode, whereas when the second program is selected, the supine bed 7 is caused to transition to the power saving mode. However, when the first program is selected, all the devices (e.g., the FPD 6b in addition to the upright stand 8) except for the device used in control by the program may be caused to transition to the power saving mode. In addition, when the second program is selected, all the devices (e.g., the FPD 6a in addition to the supine bed 7) except for the device used in control by the program may be caused to transition to the power saving mode.

Note that a plurality of units or apparatuses according to the present embodiment may be implemented by processors or processing circuitry. The processing circuitry may be constituted of a singular set of circuitry such as a CPU, plural sets of circuitry corresponding to each of the units, or the combination thereof.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A medical imaging apparatus comprising:
   an anode rotating type X-ray tube configured to generate X-rays;
   a high voltage generation unit implemented by circuitry configured to generate a high voltage to be applied to the X-ray tube;
   a power supply unit implemented by circuitry configured to supply power to the high voltage generation unit implemented by circuitry; and
   a control unit implemented by circuitry configured to control the high voltage generation unit to stop or start supply of a filament current to the X-ray tube and/or supply of a current to a stator coil for anode rotation in accordance with a predetermined rule,
   wherein the control unit stops supply of power from the power supply unit to the high voltage generation unit after a main switch of the power supply unit is turned on.

2. The medical imaging apparatus of claim 1, wherein the control unit starts supply of a filament current to the X-ray tube a first time before an examination start time in accordance with the predetermined rule.

3. The medical imaging apparatus of claim 2, wherein the control unit starts supply of a current to the stator coil a second time before the examination start time in accordance with the predetermined rule.

4. The medical imaging apparatus of claim 3, wherein the second time is shorter than the first time.

5. The medical imaging apparatus of claim 4, wherein the control unit stops supply of power from the power supply unit to the high voltage generation unit since a main switch of the power supply unit is turned on, and starts supply of power from the power supply unit to the high voltage generation unit before the first time.

6. The medical imaging apparatus of claim 1, wherein the control unit stops supply of power from the power supply unit to the high voltage generation unit when a period in which there is no person in an examination room in which the medical imaging apparatus is installed exceeds a predetermined time.

7. The medical imaging apparatus of claim 1, wherein the control unit starts supply of power from the power supply unit to the high voltage generation unit before a predetermined time.

8. The medical imaging apparatus of claim 1, configured as a biplane type apparatus, wherein
the X-ray tube is more than one,
the high voltage generation unit is more than one and corresponds to said more than one X-ray tube, respectively,
the power supply unit is configured to supply power to said more than one high voltage generation unit,
the control unit is configured to control said more than one high voltage generation unit to selectively supply a filament current to said more than one X ray tube and/or supply a current to the stator coil for anode rotation.

9. A medical imaging apparatus comprising:
an anode rotating type X-ray tube configured to generate X-rays;
a high voltage generation unit implemented by circuitry configured to generate a high voltage to be applied to the X-ray tube;
a power supply unit implemented by circuitry configured to supply power to the high voltage generation unit; and
a control unit implemented by circuitry configured to control supply/stop of a current from the power supply unit to the high voltage generation unit in accordance with a predetermined rule,
wherein the control unit stops supply of power from the power supply unit to the high voltage generation unit after a main switch of the power supply unit is turned on.

10. The medical imaging apparatus of claim 9, further comprising:
a plurality of devices configured to operate in response to supply of power from the power supply unit; and
a memory configured to store, in association with each of the plurality of devices, transition conditions for transition from a normal mode to a power saving mode, wherein consumption of the power supplied from the power supply unit is smaller in the power saving mode than in the normal mode, the transition conditions including at least a condition that at least one examination program is selected, and a condition that processing other than processing performed during a period from an input of examination start instruction to a completion of storing obtained medical image data is being executed,
wherein the control unit controls, in response to one of the transition conditions being satisfied, one or more of the plurality of devices associated with the satisfied condition to transition into the power saving mode.

11. The medical imaging apparatus of claim 9, wherein the control unit starts supply of power from the power supply unit to the high voltage generation unit before a predetermined time.

12. The medical imaging apparatus of claim 9, configured as a biplane type apparatus, wherein
the X-ray tube is more than one,
the high voltage generation unit is more than one and corresponds to said more than one X-ray tube, respectively,
the power supply unit is configured to supply power to said more than one high voltage generation unit,
the control unit is configured to control supply/stop of a current from the power supply unit to said more than one high voltage generation unit in accordance with a predetermined rule.

* * * * *